US010299318B2

(12) United States Patent
Dalhielm et al.

(10) Patent No.: US 10,299,318 B2
(45) Date of Patent: May 21, 2019

(54) DETECTING LEAKAGE WHEN HEATING A PERISHABLE DIELECTRIC LOAD

(71) Applicant: ANTRAD MEDICAL AB, Kista (SE)

(72) Inventors: Oskar Dalhielm, Upplands Väsby (SE);
Pierre Westin, Täby (SE); Lars Ekemar, Södertälje (SE); Kari Munukka, Äkersberga (SE)

(73) Assignee: ANTRAD MEDICAL AB, Kista (SE)

( * ) Notice: Subject to any disclaimer, the term of this patent is extended or adjusted under 35 U.S.C. 154(b) by 372 days.

(21) Appl. No.: 15/312,815

(22) PCT Filed: May 5, 2015

(86) PCT No.: PCT/SE2015/050495
§ 371 (c)(1),
(2) Date: Nov. 21, 2016

(87) PCT Pub. No.: WO2015/190974
PCT Pub. Date: Dec. 17, 2015

(65) Prior Publication Data
US 2017/0188415 A1    Jun. 29, 2017

(30) Foreign Application Priority Data

Jun. 10, 2014 (SE) ...................... 1450703

(51) Int. Cl.
*H05B 6/64* (2006.01)
*H05B 6/62* (2006.01)
(Continued)

(52) U.S. Cl.
CPC .............. *H05B 6/50* (2013.01); *A61M 5/445* (2013.01); *H05B 6/62* (2013.01); *H05B 6/6408* (2013.01);
(Continued)

(58) Field of Classification Search
CPC ........ H05B 6/50; H05B 6/6408; H05B 6/705; H05B 6/80; H05B 6/62; H05B 6/6494; A61M 5/445; A61M 2205/3686
(Continued)

(56) References Cited

U.S. PATENT DOCUMENTS 3,518,393 A * 6/1970 Bull ...................... A61M 5/445
                                                        219/772
4,503,307 A * 3/1985 Campbell ............. A61M 5/445
                                                        219/736
4,801,777 A    1/1989 Auerbach

FOREIGN PATENT DOCUMENTS

DE    19726625 A1    12/1998
EP    0261007 A1     3/1988
(Continued)

OTHER PUBLICATIONS

European Search Report for PCT/SE2015050495 dated Jan. 23, 2018.
(Continued)

*Primary Examiner* — Quang T Van
(74) *Attorney, Agent, or Firm* — Moore & Van Allen PLLC; W. Kevin Ransom

(57) ABSTRACT

A cartridge holds a perishable dielectric load, e.g. blood plasma, during heating n a heating chamber by means of an electromagnetic field from an emitting element. A conducting container of the cartridge is arranged between the emitting element and the perishable dielectric load. The conducting container holds dielectric matter and is arranged in contact with a load container for the perishable dielectric load, so that energy from the electromagnetic field is bridged into the perishable dielectric load. A first surface of the cartridge faces the emitting element and contains a recess for receiving any fluid having leaked out from the conducting container and/or the load container. A transmitter module for
(Continued)

generating the electromagnetic energy repeatedly measures an impedance of the perishable dielectric load and the conducting container. If, due to any fluid being located in the recess, the impedance deviates substantially from a previous measurement, an alarm signal is generated.

12 Claims, 2 Drawing Sheets

(51) Int. Cl.
    *A61M 5/44*     (2006.01)
    *A61M 1/02*     (2006.01)
    *H05B 6/50*     (2006.01)
    *H05B 6/70*     (2006.01)
    *H05B 6/80*     (2006.01)

(52) U.S. Cl.
    CPC ........... *H05B 6/6494* (2013.01); *H05B 6/705* (2013.01); *H05B 6/80* (2013.01); *A61M 2205/3686* (2013.01)

(58) Field of Classification Search
    USPC ....... 219/779, 774, 772, 759, 762, 385, 438, 219/687; 604/114, 113, 409, 246, 317, 604/913; 210/177, 187, 198.1; 426/107, 426/415, 412, 234
See application file for complete search history.

(56) References Cited

FOREIGN PATENT DOCUMENTS

| WO | 9636200 A1 | 11/1996 |
| WO | 0035251 A1 | 6/2000 |
| WO | 02054833 A1 | 7/2002 |
| WO | 2011145994 A1 | 11/2011 |
| WO | 2013159815 A1 | 10/2013 |

OTHER PUBLICATIONS

International Search Report for PCT/SE2015/050495 dated Mar. 9, 2015.
Written Opinion of the International Search Authority for PCT/SE2015/050495 dated Mar. 9, 2015.

\* cited by examiner

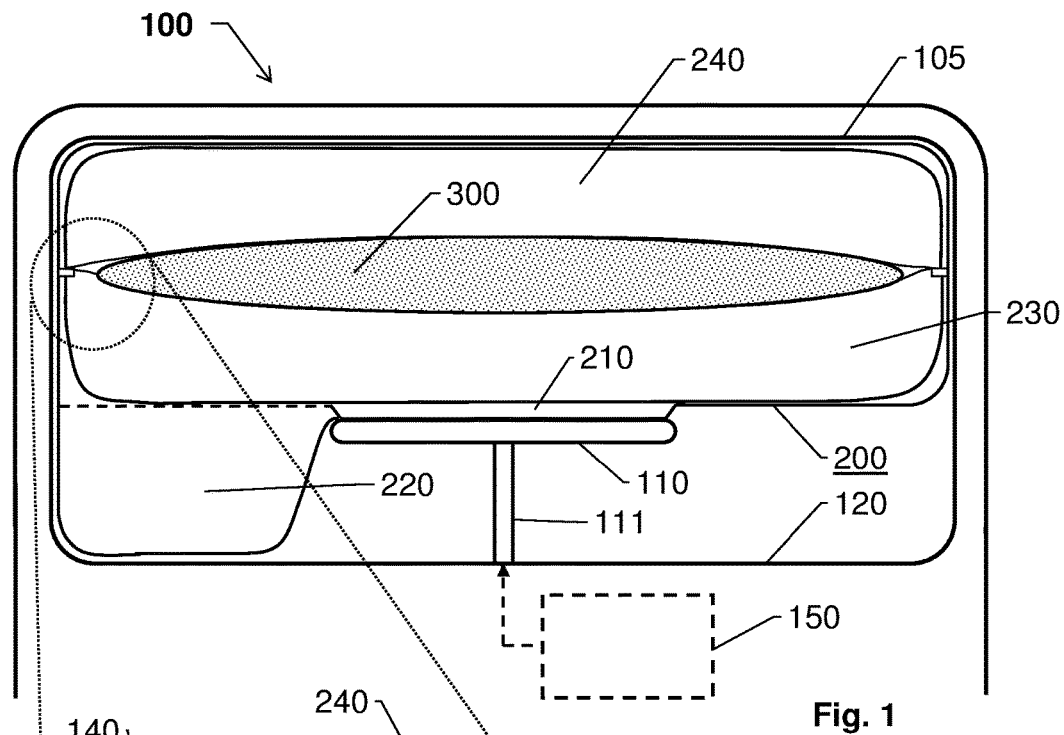
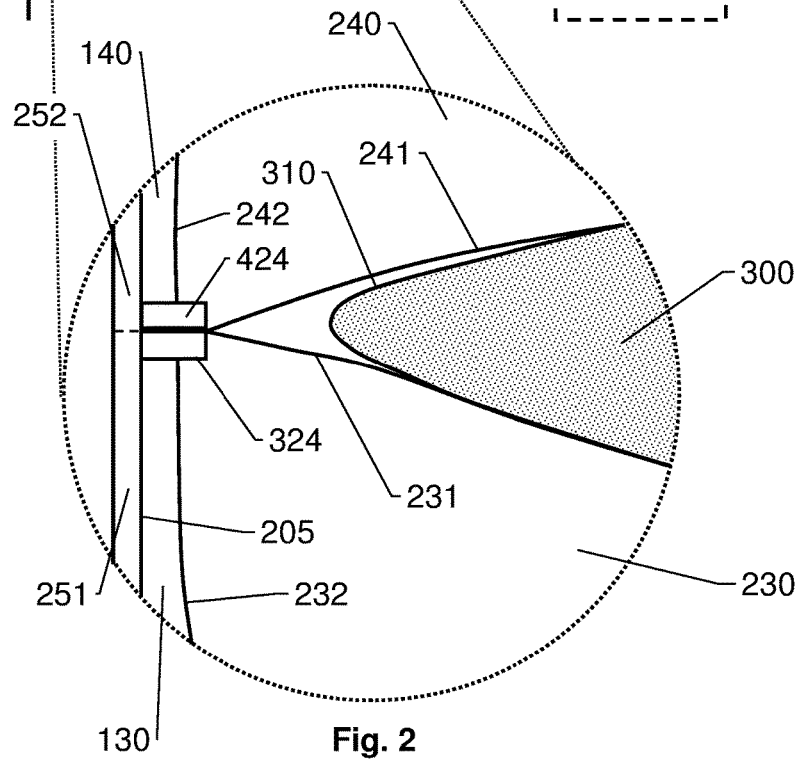

DETECTING LEAKAGE WHEN HEATING A PERISHABLE DIELECTRIC LOAD

CROSS-REFERENCE TO RELATED APPLICATION(s)

This application is a national stage application (filed under 35 § U.S.C. 371) of PCT/SE2015/050495, filed May 5, 2015 of the same title, which, in turn claims priority to Swedish Application No. 1450703-2, filed Jun. 10, 2014 of the same title; the contents of each of which are hereby incorporated by reference.

FIELD OF THE INVENTION

The present invention relates generally to heating of perishable substances by means of electromagnetic fields. More particularly the invention relates to a cartridge configured to hold a perishable dielectric load during heating thereof in a heating chamber by means of an electromagnetic field.

BACKGROUND OF THE INVENTION

There are many situations in which a substance is to be heated or thawed from a first temperature (e.g. below zero degrees Celsius) to a second temperature (e.g. room temperature). Sometimes it is also important that this heating is effected quickly and at very high precision, i.e. uniformly and without overheating any parts of the substance. In such cases, the heating task may become very challenging. Heating frozen blood plasma to a temperature suitable for introduction into the human body is one example of such heating. However, of course, both within and outside the medical field there are numerous other examples of demanding heating tasks.

WO 02/054833 shows an appliance for equalizing an electromagnetic field, which is not generated in a resonant cavity, and wherein a dielectric load being heated contains matters with one or more dielectric constants and loss factors.

WO 2011/145994 discloses another solution for equalizing a warming process wherein a load is heated via an electromagnetic field. Here, the load is surrounded by a field equalizing material. The load and the electromagnetic field are also moved relative to one another in order to enhance the heating process and render it more energy distribution more uniform.

WO 2011/159815 describes a solution according to which a dielectric load is heated from an initial temperature level to a desired final temperature level by using alternating electromagnetic energy from an energy source, which produces a predefined set of spectral components. A cavity contains the dielectric load, and an antenna transmits an electromagnetic field through the dielectric load. Mechanical processing means cause a relative movement between the dielectric load and the at least one antenna, thus varying a spatial relationship between the alternating electromagnetic field and the dielectric load. As a result, the electromagnetic energy is distributed relatively evenly in the dielectric load. Sensor means register a temperature level of the dielectric load; and based thereon an amount of energy is transmitted through the dielectric load.

Consequently, various solutions are known for heating a dielectric load by using an electromagnetic field, and for example surrounding the load by a field equalizing material to enhance the heating process. Nevertheless, there is yet no solution to automatically detect any leakage from the load or the surrounding material during the heating. Leakage of this type not only risks damaging the load as such, however also the heater might be damaged, or at least require significant cleaning due to the substances having escaped from the load and/or the equalizing material.

SUMMARY OF THE INVENTION

The object of the present invention is therefore to solve the above problem, and thus offer a simple and reliable means for detecting any leaking liquid originating from either of the perishable dielectric load, the conducting container surrounding the load, or both.

According to one aspect of the invention, the object is achieved by the initially described cartridge, having a first surface configured to face the emitting element when being positioned in the heating chamber. The first surface contains a recess configured to receive any fluid having leaked out from the at least one conducting container and/or the load container.

This cartridge is advantageous because any leaking fluid will be accumulated in the recess, where it, due to its location in front of the emitting element, can easily be detected via for example impedance measurements performed during the heating process.

Preferably, the dielectric matter in the at least one conducting container has a dielectric constant matching a dielectric constant of the perishable dielectric load in such a manner that the energy of the electromagnetic field is conducted to the perishable dielectric load with minimal heat dissipation into the dielectric matter. This criterion is for example fulfilled if the perishable dielectric load preferably contains a blood product, and the dielectric matter comprises deionized water.

According to one preferred embodiment of this aspect of the invention, the conducting container is arranged with a spacing to at least one inner wall of the cartridge. The spacing is configured to allow any fluid having leaked out from the conducting container and/or the load container to be transported by gravity towards the recess. Thus, the possibility to detect also very small amounts of leaking fluid is improved.

According to another preferred embodiment of this aspect of the invention, the cartridge includes a set of first distance elements configured to hold the conducting container at a distance from at least one first inner wall of the cartridge, which at least one first inner wall is essentially parallel to the first surface. Thereby, the chances of detecting small amounts of leaking fluid are further improved.

According to yet another preferred embodiment of this aspect of the invention, the cartridge includes a set of second distance configured to hold the conducting container at a distance from at least one second inner wall of the cartridge, which at least one second wall is essentially perpendicular to the first surface. Of course, this improves the detection chances additionally.

According to still another preferred embodiment of this aspect of the invention, a subset of the distance elements in the set of second distance elements include a respective attachment member configured hold the conducting container in a fixed position inside the cartridge. Consequently, the design can be made relatively compact and cost efficient.

According to a further preferred embodiment of this aspect of the invention, the cartridge also has a collecting compartment configured to accumulate excessive fluid, which, in turn, has overflown the recess, the conducting container and/or the load container. Thereby, the need to clean the heater can be minimized, even if the cartridge is not immediately taken out from the heater in response to a detected leakage. Namely, any excessive fluid will remain safely in the collecting compartment.

According to another preferred embodiment of this aspect of the invention, the cartridge contains first and second modules, which are pivotably fixed to one another along one side of the cartridge in such a manner that an interior thereof is accessible for installing or removing the load container when the first and second modules are arranged in an open position. This is advantageous because it facilitates a convenient use of the cartridge as a holder for the load container in a heater.

Preferably, for further enhanced user friendliness, the cartridge also has first and second conducting containers, wherein the first module contains a first conducting container, and the second module contains a second conducting container. When the first and second modules are arranged in the open position, a space is available which is configured to receive the load container between the first and second conducting containers.

According to another aspect of the invention, the object is achieved by the heater described initially, wherein the heating chamber is configured to receive and contain the proposed cartridge, which, in turn, holds the perishable dielectric load to be thawed/warmed.

Preferably, the heater has a transmitter module connected to the emitting element, and the heater is configured to operate as follows. Electromagnetic energy having predefined spectral properties is generated. An impedance of the perishable dielectric load and the conducting container is measured repeatedly. In response thereto, the spectral properties of the generated electromagnetic energy are adjusted aiming to match the measured impedance. If a required adjustment exceeds a threshold (i.e. due fluid having leaked out into the recess of the cartridge in front of the emitting element) an alarm signal is generated.

The advantages of this heater, as well as the preferred embodiments thereof, are apparent from the discussion above with reference to the proposed system.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

FIG. 1 shows a schematic side view of a heater and a cartridge according to one embodiment of the invention;

FIG. 2 shows an enlarged view of certain elements in FIG. 1; and

DETAILED DESCRIPTION OF THE INVENTION

Figure 3:
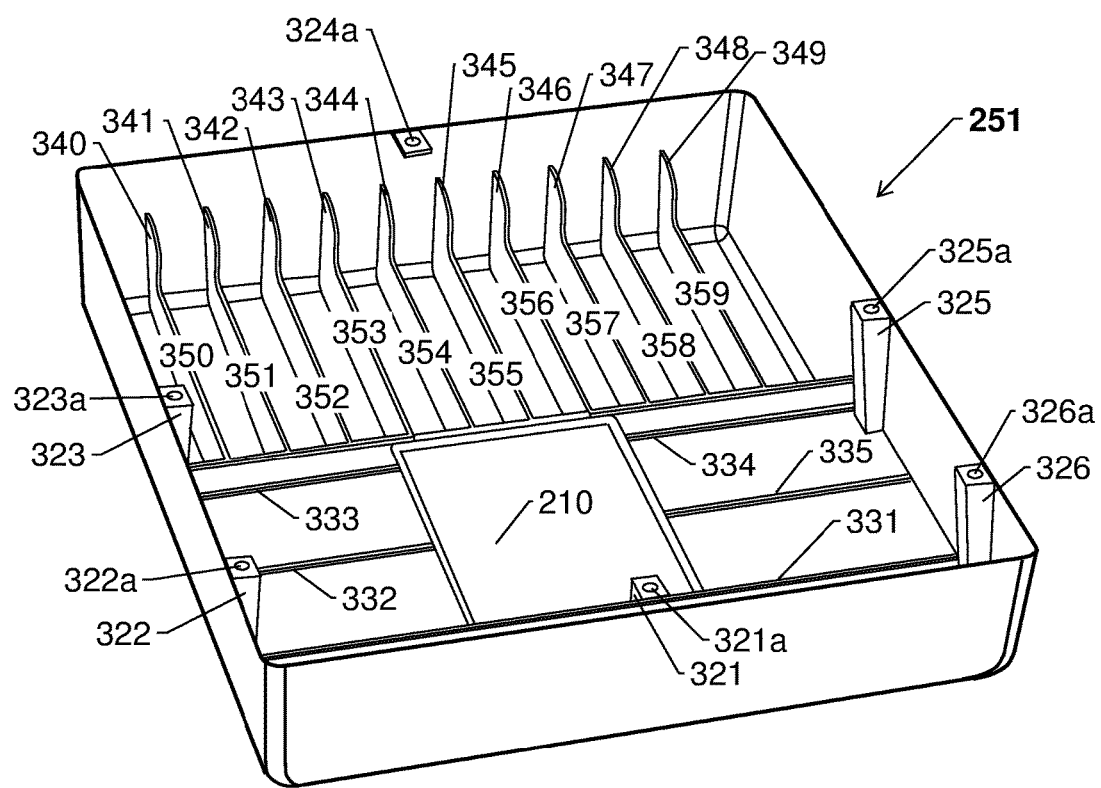
FIG. 3 shows a perspective view of a lower part of a cartridge according to one embodiment of the invention.

FIG. 1 shows a schematic side view of a heater 100 and a cartridge 200 according to one embodiment of the invention, and FIG. 2 shows an enlarged view of certain elements in FIG. 1.

The cartridge 200 is configured to hold a perishable dielectric load 300 (e.g. blood plasma) during heating thereof in a heating chamber 105 of the heater 100. The heater 100 is designed to thaw/warm the perishable dielectric load 300 by producing an electromagnetic field in the heating chamber 105 via an emitting element 110. The heating chamber 105 is specifically configured to receive and contain the cartridge 200, which, in turn, holds the perishable dielectric load 300 to be thawed/warmed.

The cartridge 200 includes a first conducting container, which is arranged between the emitting element 110 for the electromagnetic field and the perishable dielectric load 300. In the embodiment of FIG. 1, the cartridge 200 also includes a second conducting container, which is arranged above the perishable dielectric load 300, i.e. on the opposite side relative to the emitting element 110.

Here, the first conducting container is delimited by flexible surfaces 231 and 232 respectively, and the second conducting container is delimited by flexible surfaces 241 and 242 respectively. The first conducting container holds dielectric matter 230 (e.g. deionized water) and is configured to contact a load container 310 (e.g. a plastic bag) holding the perishable dielectric load 300, so as to bridge energy from the electromagnetic field into the perishable dielectric load 300. Analogously, the second conducting container holds dielectric matter 240 between the flexible surfaces 241 and 242. Further, the dielectric matter 230 and 240 preferably has a dielectric constant matching a dielectric constant of the perishable dielectric load 300, such that the energy of the electromagnetic field is conducted to the perishable dielectric load 300 with minimal heat dissipation into the dielectric matter 230 or 240.

The cartridge 200 has a first surface configured to face the emitting element 110 when the cartridge 200 is positioned in the heating chamber 105. Specifically, it is presumed that the cartridge 200 is to be arranged in the heating chamber 105, such that first surface is located above the emitting element 110. Namely, the first surface contains a recess 210 configured to receive any fluid having leaked out either from the first conducting container, the second conducting container and/or the load container 310 and has been transported to the recess 210 by gravity. Preferably, the recess 210 has such geometric properties that when the cartridge 200 is fitted into the heating chamber 105, the recess 210 is located immediately in front of the emitting element 110.

The heater 100 has a transmitter module 150 connected to the emitting element 110. The transmitter module 150 is configured to: (a) generate electromagnetic energy having predefined spectral properties; (b) measure, repeatedly, an impedance of the perishable dielectric load 300 and the conducting containers, and in response thereto, adjust the spectral properties of the generated electromagnetic energy aiming to match the measured impedance. Thereby, it is ensured that the energy transfer to the perishable dielectric load 300 is made efficient. However, if the required adjustment exceeds a threshold, the transmitter module 150 is configured to generate an alarm signal. Here, the alarm signal is indicative of a leakage. Namely, it is presumed that the impedance mismatch is due to the fact that the recess 210 contains fluid originating from conducting container(s) and/or the load container 310.

Referring now to FIG. 2, according to one preferred embodiment of the invention, each of the first and second conducting containers is arranged with a spacing 130 and 140 respectively to at least one inner wall 205 of the cartridge 200. The spacing 130 and 140 is configured to allow any fluid having leaked out from any of the conducting containers and/or the load container 310 to be transported by gravity towards the recess 210, i.e. between the respective conducting container and the inner wall 205, and further via the first surface into the recess 210.

Moreover, it is advantageous if the cartridge 200 contains a collecting compartment 220, which is configured to accumulate excessive fluid having overflown the recess 210, or emanating directly from the conducting containers and/or the load container 310. To this aim, the collecting compartment 220 preferably has relatively large capacity, and is arranged in a lowermost part of the cartridge 200 as illustrated in FIG. 1. Thereby, it is not required that the cartridge 200 be removed immediately from the heater 100 if a leakage is detected. Namely, any excessive fluid will remain safely in the collecting compartment 220.

According to one preferred embodiment of the invention, the cartridge 200 contains first and second modules 251 and 252 respectively, which are pivotably fixed to one another along one side of the cartridge 200. Thus, the first and second modules 251 and 252 are interconnected via a hinge means in such a manner that an interior of the cartridge 200 is accessible for installing or removing the load container 310 when the first and second modules 251 and 252 are arranged in an open position. Further preferably, the conducting containers are arranged, such that the first module 251 (i.e. the lower part of the cartridge 200 in FIG. 2) includes the first conducting container, and the second module 252 (i.e. the upper part of the cartridge 200 in FIG. 2) contains the second conducting container. As a result, when the first and second modules 251 and 252 are arranged in the open position, a space is available there between. This space, in turn, is configured to receive the load container 310 so that when the cartridge 200 is closed, the load container 310 is fixed between the first and second conducting containers.

FIG. 3 shows a perspective view of a lower part 251 (i.e. the first module) of the cartridge 200 according to one embodiment of the invention. The first module 251 contains a set of first distance elements 331, 332, 333, 334, 335, 350, 351, 352, 353, 354, 355, 356, 357, 358 and 359 configured to hold the first conducting container at a distance from at least one respective first inner wall of the cartridge 200. The at least one first inner wall is here essentially parallel to the first surface (i.e. approximately horizontal when the cartridge 200 is installed in a heater 100 operating as intended). The set of first distance elements preferably includes a number of ribs upon which the first conducting container rests while leaving a spacing to the at least one first inner wall.

The cartridge 200 preferably also contains a set of second distance elements 321, 322, 323, 325, 326, 340, 341, 342, 343, 344, 345, 346, 347, 348 and 349 configured to hold the first conducting container at a distance from at least one respective second inner wall of the cartridge 200. The at least one second wall is essentially perpendicular to the first surface (i.e. approximately vertical when the cartridge 200 is installed in a heater 100 operating as intended). The set of second distance elements may include ribs similar to those of the first set of distance elements. However also other types of support members, such as columns are conceivable according to embodiments of the invention Nevertheless, it is advantageous if a subset 321, 322, 323, 325 and 326 of the distance elements in the set of second distance elements includes a respective attachment member 321a, 322a, 323a, 325a, 326a configured hold first conducting container in a fixed position inside the cartridge 200. Thus, the first conducting container is secured in the cartridge 200, and at the same time, it is ensured that there is a spacing 130 between the first container and the inner walls of the cartridge.

Naturally, although not shown in FIG. 3, the upper part 252 (i.e. the second module) of the cartridge 200 preferably includes elements analogous to the above-mentioned sets of first and second distance elements in order to allow any leaking fluid from the second conducting container to pass in the spacing 140 between the second conducting container and the inner wall of the cartridge 200.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A cartridge configured to hold a perishable dielectric load during heating thereof in a heating chamber by means of an electromagnetic field, the cartridge comprising:
   at least one conducting container arranged between an emitting element for the electromagnetic field and the perishable dielectric load, the at least one conducting container holding dielectric matter and being configured to contact a load container holding the perishable dielectric load so as to bridge energy from the electromagnetic field into the perishable dielectric load; and
   a first surface configured to face the emitting element when being positioned in the heating chamber, the first surface containing a recess configured to receive any fluid having leaked out from the at least one conducting container and/or the load container.

2. The cartridge according to claim 1, wherein the at least one conducting container is arranged with a spacing to at least one inner wall of the cartridge, the spacing being configured to allow any fluid having leaked out from the at least one conducting container and/or the load container to be transported by gravity towards the recess.

3. The cartridge according to claim 2, comprising a set of first distance elements configured to hold the at least one conducting container at a distance from at least one respective first inner wall of the cartridge, which at least one first inner wall is essentially parallel to the first surface.

4. The cartridge according to claim 2, comprising a set of second distance elements configured to hold the at least one conducting container at a distance from at least one respective second inner wall of the cartridge, which at least one second wall is essentially perpendicular to the first surface.

5. The cartridge according to claim 4, wherein a subset of the distance elements in the set of second distance elements comprises a respective attachment member configured hold at least one of the at least one conducting container in a fixed position inside the cartridge.

6. The cartridge according to claim 1, comprising a collecting compartment configured to accumulate excessive fluid from at least one of the recess, the at least one conducting container and the load container.

7. The cartridge according to claim 1, wherein the dielectric matter in the at least one conducting container has a dielectric constant matching a dielectric constant of the perishable dielectric load in such a manner that the energy of the electromagnetic field is conducted to the perishable dielectric load with minimal heat dissipation into the dielectric matter.

8. The cartridge according to claim 7, wherein the perishable dielectric load comprises a blood product, and the dielectric matter comprises deionized water.

9. The cartridge according to claim 1, comprising first and second modules being pivotably fixed to one another along one side of the cartridge in such a manner that an interior thereof is accessible for installing or removing the load container when the first and second modules are arranged in an open position.

10. The cartridge according to claim 9, comprising first and second conducting containers, and wherein:
the first module comprises the first conducting container,
the second module comprises the second conducting containers, and
when the first and second modules are arranged in the open position, a space is available which space is configured to receive the load container between the first conducting container and the second conducting container.

11. A heater for thawing/warming a perishable dielectric load, the heater comprising:
a heating chamber; and
an emitting element configured to produce an electromagnetic field in the perishable dielectric load,
wherein the heating chamber is configured to receive and contain a cartridge comprising:
at least one conducting container arranged between the emitting element for the electromagnetic field and the perishable dielectric load, the at least one conducting container holding dielectric matter and being configured to contact a load container holding the perishable dielectric load so as to bridge energy from the electromagnetic field into the perishable dielectric load; and
a first surface configured to face the emitting element when being positioned in the heating chamber, the first surface containing a recess configured to receive any fluid having leaked out from the at least one conducting container and/or the load container.

12. The heater according to claim 11, comprising a transmitter module connected to the emitting element and configured to:
generate electromagnetic energy having predefined spectral properties;
measure, repeatedly, an impedance of the perishable dielectric load and the at least one conducting container, in response thereto;
adjust the spectral properties of the generated electromagnetic energy aiming to match the measured impedance; and if and adjustment exceeds a threshold is required generate an alarm signal.

* * * * *